US00PP20699P3

(12) United States Plant Patent
Skelton

(10) Patent No.: US PP20,699 P3
(45) Date of Patent: Feb. 2, 2010

(54) KIWI PLANT NAMED 'SKELTON X78'
(50) Latin Name: *Actinidia chinensis*
Varietal Denomination: Skelton X78

(75) Inventor: Donald Skelton, Huntly (NZ)

(73) Assignee: Enza Limited, Mt. Wellington (NZ)

( * ) Notice: Subject to any disclaimer, the term of this patent is extended or adjusted under 35 U.S.C. 154(b) by 0 days.

(21) Appl. No.: 12/005,037

(22) Filed: Dec. 21, 2007

(65) Prior Publication Data

US 2008/0184400 P1 Jul. 31, 2008

(51) Int. Cl.
*A01H 5/00* (2006.01)

(52) U.S. Cl. ..... Plt./156
(58) Field of Classification Search ..... Plt./156
See application file for complete search history.

*Primary Examiner*—Annette H Para
(74) *Attorney, Agent, or Firm*—Black Lowe & Graham PLLC

(57) ABSTRACT

A new and distinct kiwi plant of the species *Actinidia chinensis* is described. The cultivar results from a controlled pollination using a male *A. chinensis* selection 'RY,' and a female *A. chinensis* selection 'A124.' Both named parents ('RY' and 'A124') are unpatented cultivars. The new cultivar is distinguished by its medium fruit size, ovoid fruit shape, greenish-yellow fruit coloring, and its medium harvest date in late April.

6 Drawing Sheets

FIELD OF THE INVENTION

Genus and species of plant claimed: *Actinidia chinensis.*

PRIORITY CLAIM

The present application claims priority from New Zealand Plant Variety Rights Application, entitled 'Skelton X78' filed Dec. 22, 2006, with the Commissioner of Plant Variety Rights in New Zealand, which is herein incorporated by reference.

BACKGROUND OF THE INVENTION

Kiwi plants in cultivation are mainly varieties of *A. deliciosa,* particularly 'Hayward' although some *A. chinensis* and *A. arguta* varieties are grown. *A. deliciosa* and *A. chinensis* are closely related and varieties of both types have large fruit (about 100 g) with hair on the skin. The main varieties in New Zealand are 'Hayward' (*A. deliciosa*) and 'HORT16A' (*A. chinensis*). Fruit are usually cut and eaten with a spoon.

All *Actinidia* species are dioecious, so female varieties have to be interplanted with male pollinizers to ensure fruit production.

*A. chinensis* vines are deciduous and tend to grow vigorously in spring and summer when rapidly-growing shoots can intertwine and tangle if not managed. Vines do best in a mild warm-temperate climate without late spring or early autumn frosts. They produce consistently heavy crops when grown in well-drained fertile soils and given regular irrigation in dry spells.

*A. chinensis* flowers in late September to late October in New Zealand. Harvest of *A. chinensis* fruit occurs from late February to late June in New Zealand depending on the selection and location of plantings.

SUMMARY OF THE INVENTION

The present invention is a new and distinctive kiwifruit variety having a medium sized ovoid fruit shape, a vegetative bud break of mid-August, a flowering date of early October, and a fruit harvest date of early April. This new variety is designated 'Skelton X78' and is derived from a controlled pollination using a female *A. chinensis* selection 'A124' and a male *A. chinensis* selection 'RY.'

Neither of the parents are registered with the Plant Variety Rights Office in New Zealand or patented. The parent plants are part of an ongoing breeding program established in New Zealand in 1975.

This new variety was created during the course of a planned plant-breeding program, which was initiated in Waiuku, New Zealand in 1994 and approximately 300 seedlings were raised at Rangiriri, New Zealand. 'Skelton X78' first flowered in 1999 and fruit were assessed in 2000. Following fruit assessment, 'Skelton X78' was grafted onto three *Actinidia deliciosa* seedling rootstocks and onto three *Actinidia chinensis* seedling rootstocks. The unique characteristics of 'Skelton X78' continued and the asexually reproduced plants were true to type.

The new variety can be asexually reproduced as cuttings or by grafting or budding on to seedling or cutting-grown rootstocks of *A. deliciosa* or *A. chinensis,* or by striking cuttings, or by tissue culture. Trial plantings of grafted plants established in Rangiriri, New Zealand in 2000 have shown that the unique combination of characteristics, observed with the first mature fruit of 2000, come true to form, are established, and transmitted through succeeding asexual propagations. The photographs included were taken in April 2006 and are of plants grafted in July 1999.

'Skelton X78' flowers a week to two weeks earlier than 'HORT16A' and the fruit reaches maturity in late April several weeks earlier than 'HORT16A' which reach maturity in early May.

COMPARISON TO CLOSEST VARIETY

Figure 1:
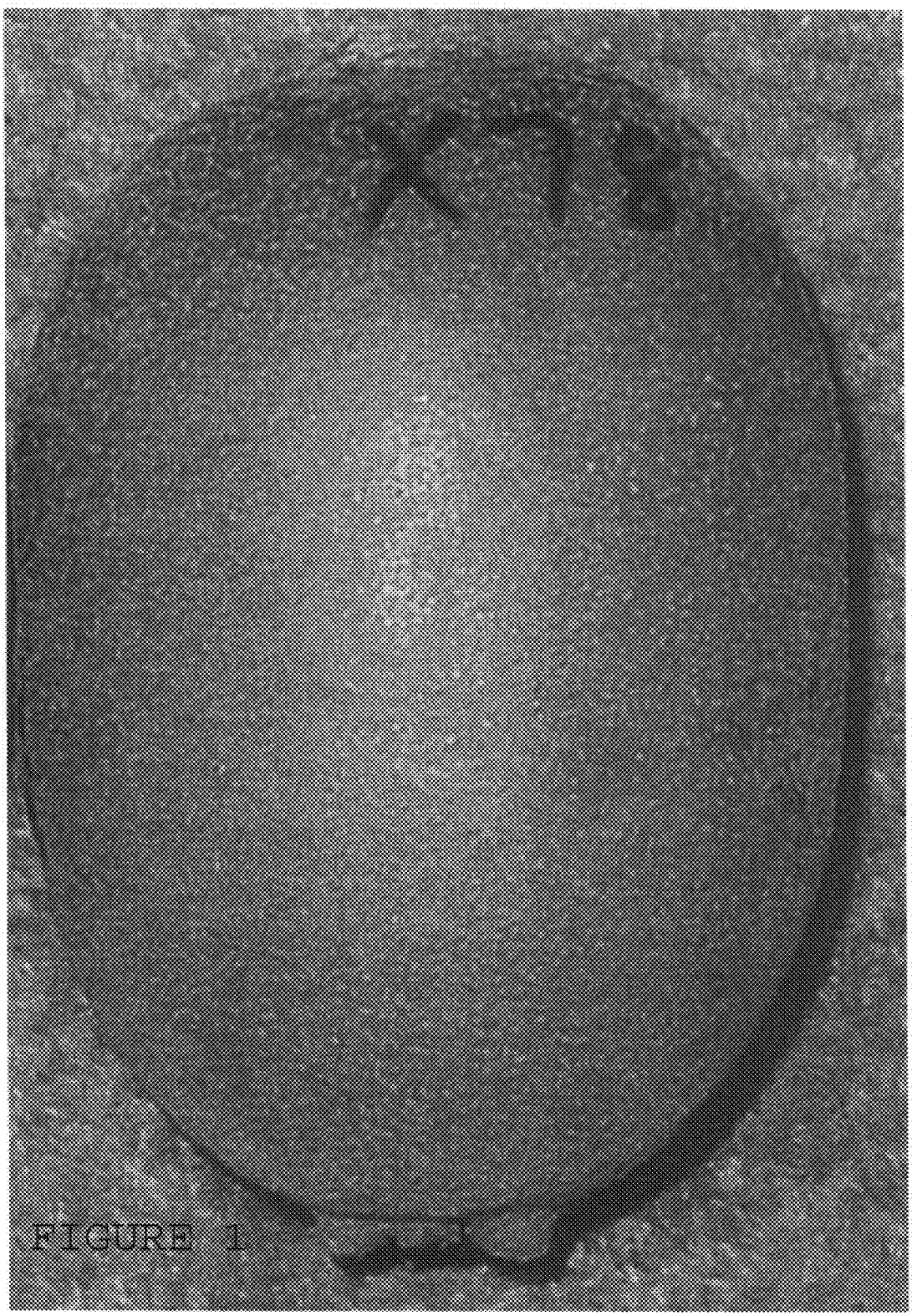
FIG. 1 shows typical fruit of the new variety in the studio.
Figure 2:
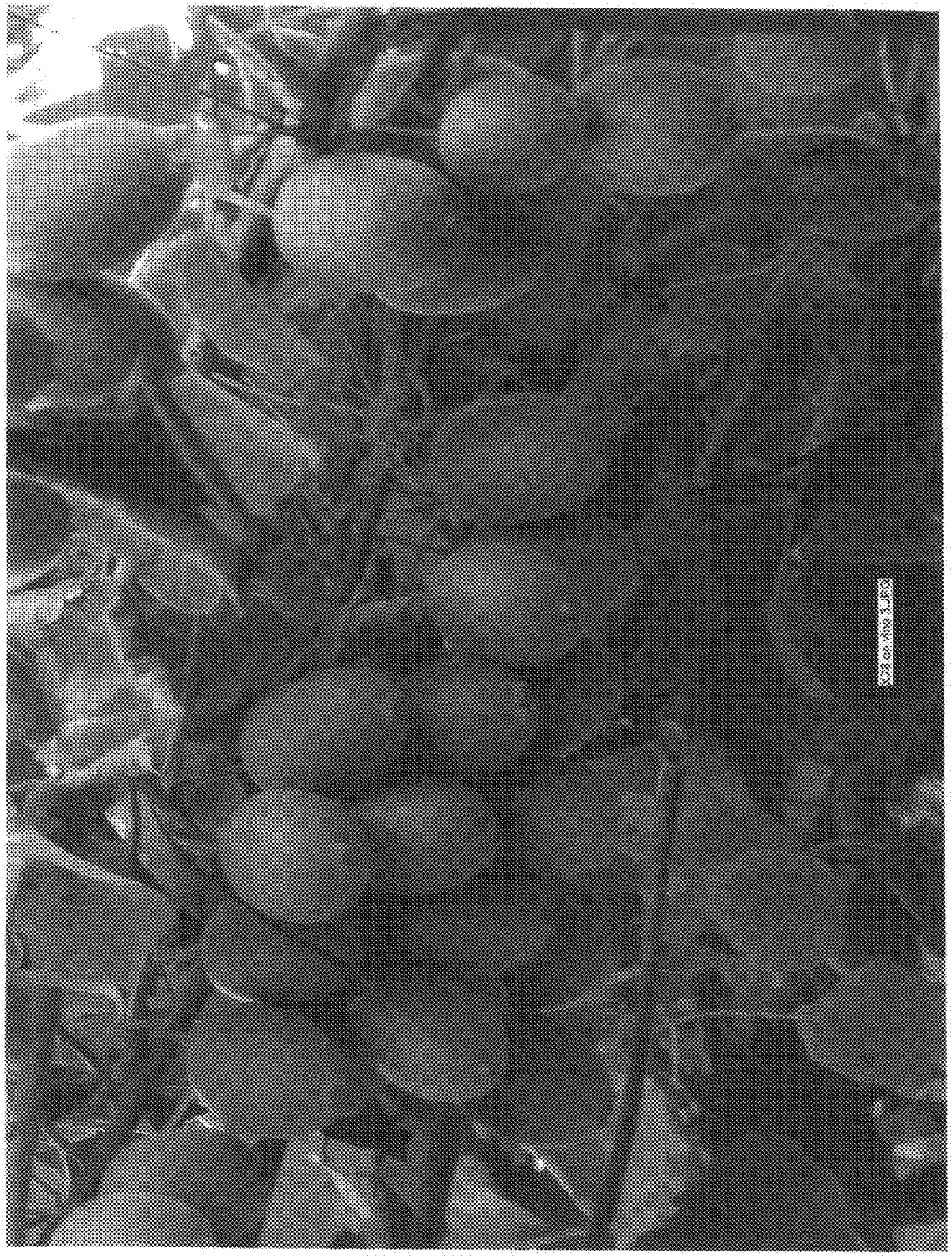
FIG. 2 shows typical fruit of the new variety in the orchard.
Figure 3:
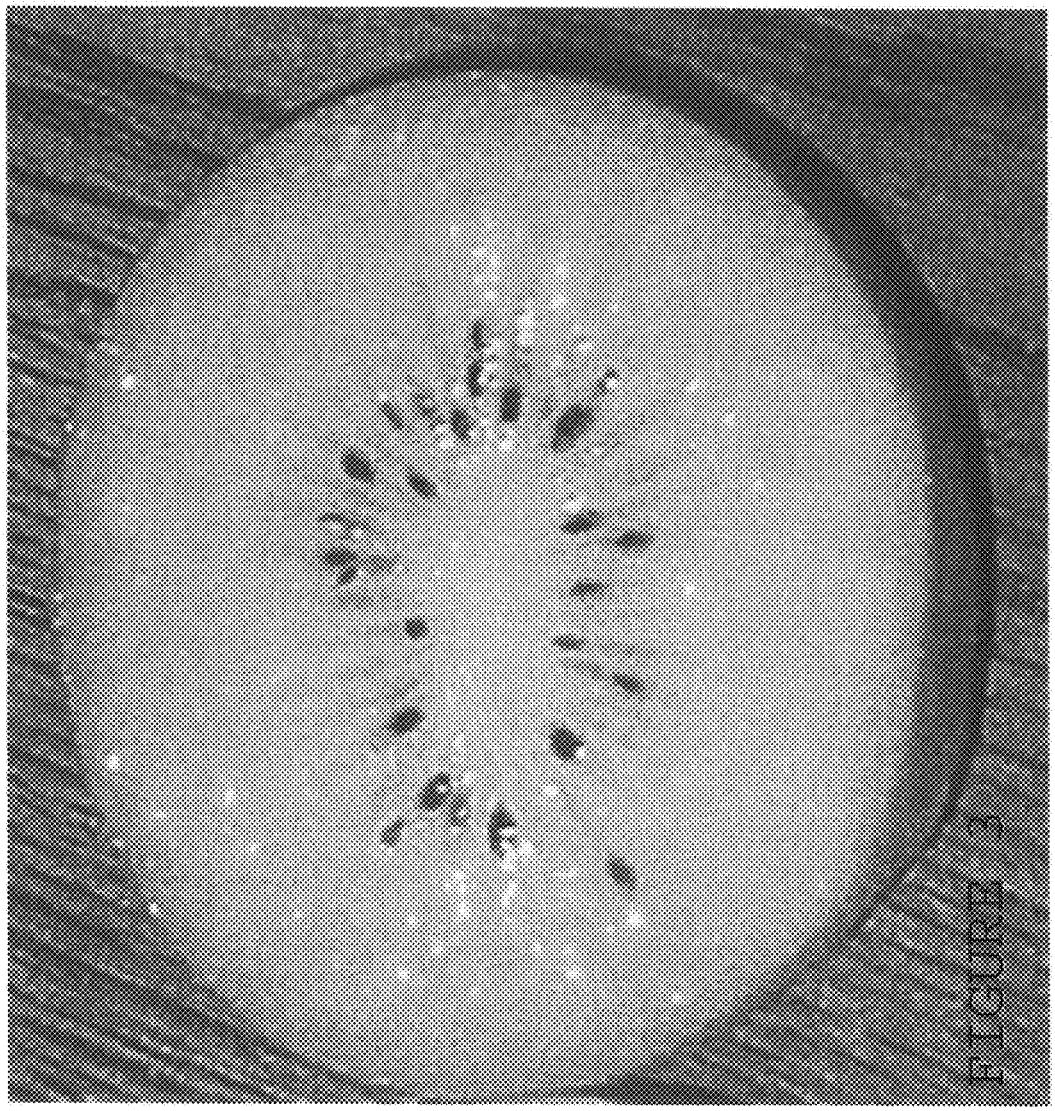
FIG. 3 shows fruit of the new variety in cross-section.
Figure 4:
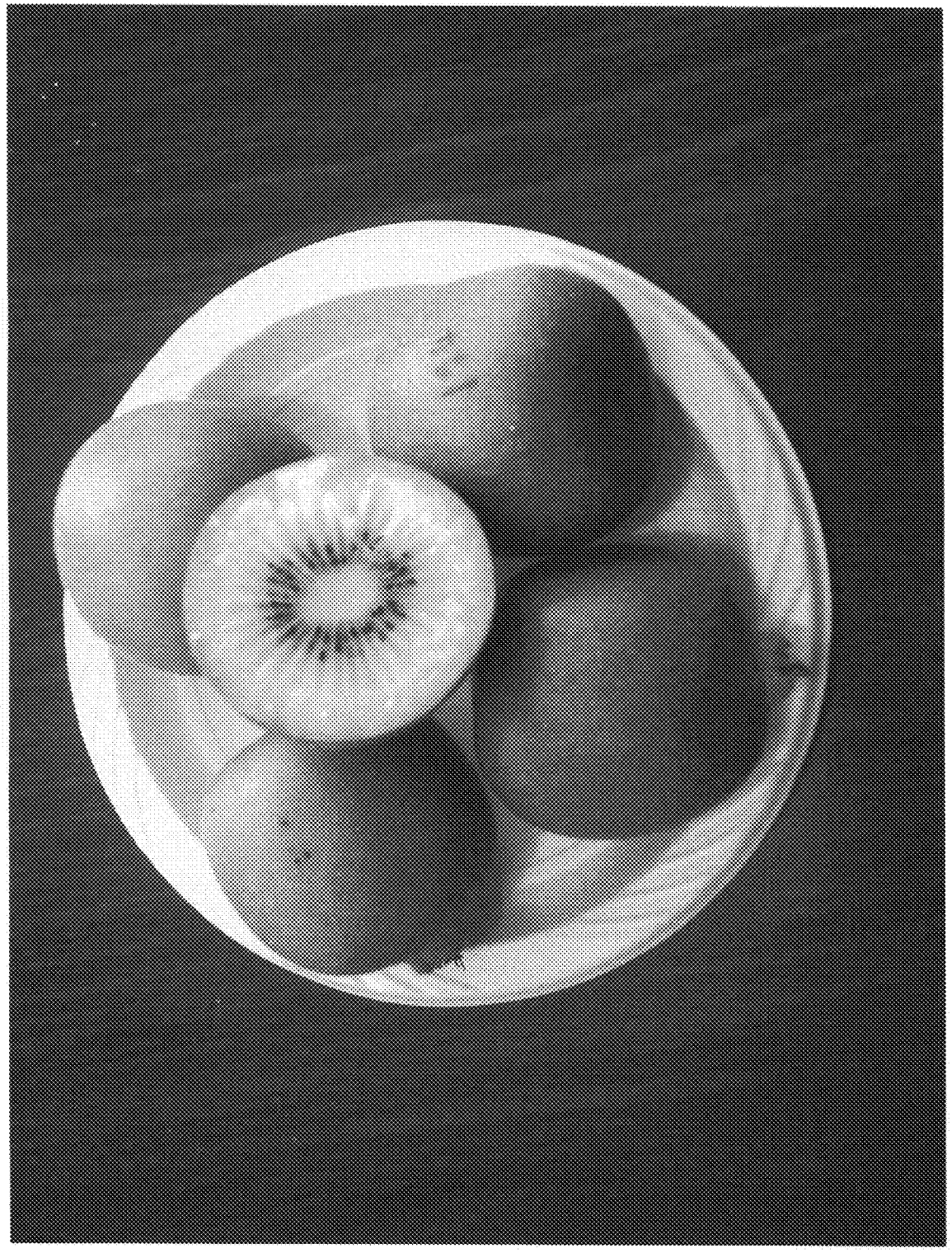
FIG. 4 shows typical fruit of the parent female A124 species in the studio and in cross-section.
Figure 5:
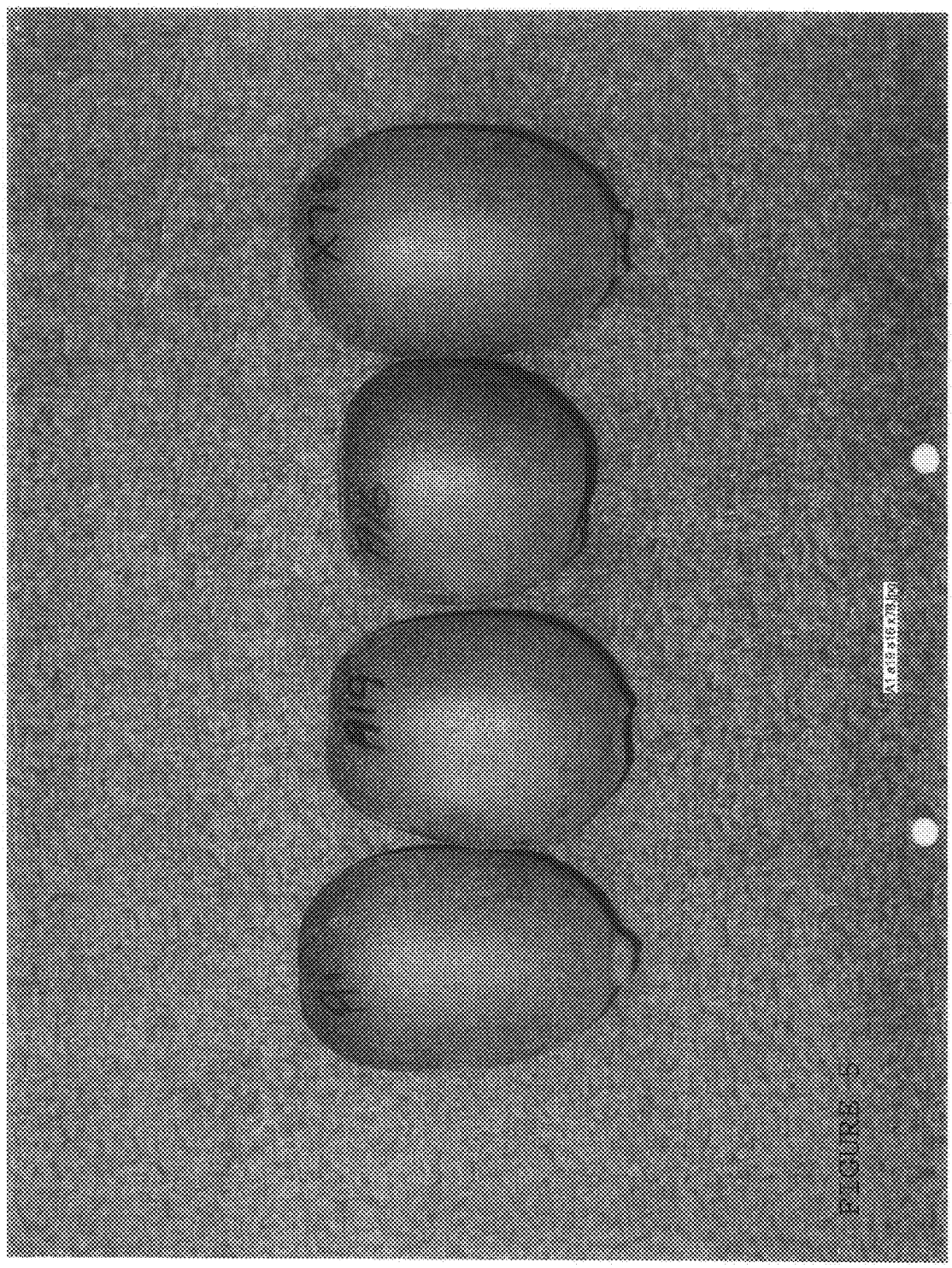
FIG. 5 shows typical fruit of the new variety in the studio compared with other varieties, in order: 'A1'; 'Skelton A19;' 'Skelton A16;' and 'Skelton X78.
Figure 6:
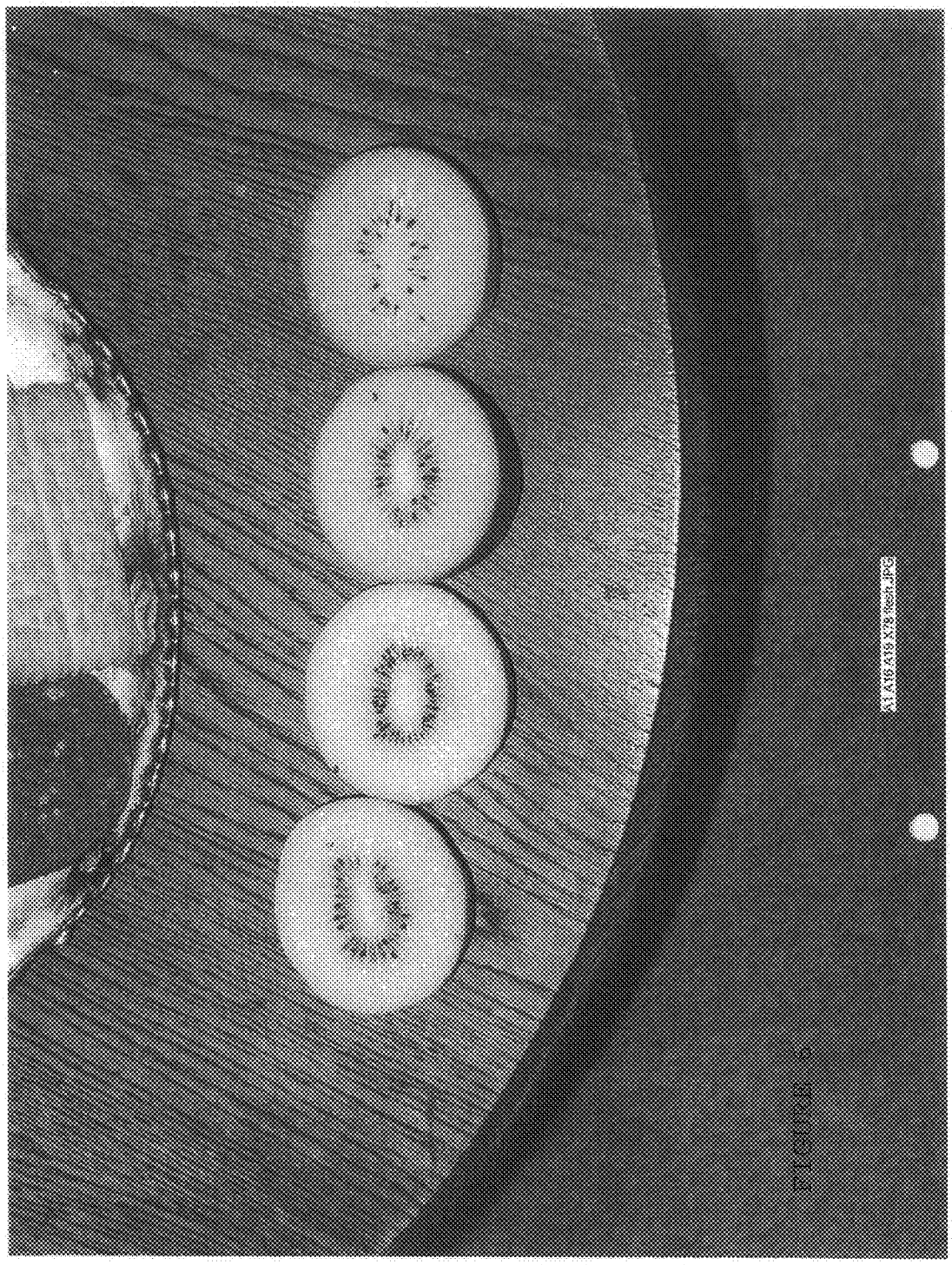
' and FIG. 6 shows typical fruit of the new variety in the studio compared with other varieties in cross-section, in order: 'A1'; 'Skelton A16;' 'Skelton A19;' and 'Skelton X78.'

The distinctive characteristics of 'Skelton X78' were first observed with the first fruit maturing in 2000. The distinctive characteristics of this new Kiwi variety, described in detail below and shown in the accompanying photographs, were observed in April 2006 at Rangiriri, New Zealand. The age of the plants was approximately six years from grafting onto seedling rootstocks.

Comparison with the similar variety 'HORT16A' (U.S. Plant Pat. No. 11,066) shows that 'Skelton X78' may be distinguished as follows in Table 1:

TABLE 1

Comparison With Similar Variety.
Observations made under New Zealand Growing Conditions

| Characteristic | HORT16A | X78 |
|---|---|---|
| FRUIT | | |
| Harvest Date | Early May | Late April |
| Color of Ripe Pericarp | Medium yellow (12C/12B) | Greenish yellow (5C) |
| Skin Color | Yellow-brown 199B | Yellow-brown 199B |
| Mean Fresh Weight | 43-176 grams | 67-93 grams |
| Mean Dry Matter at Harvest | 18% | 15.5% |
| Average Length | 79.1 mm | 75.0 mm |
| Average Width | 51.1 mm | 46.0 mm |
| Core Diameter | 12.4 mm | 12.0 mm |
| Width/Length Ratio | 0.65 | 0.65 |
| Sweetness (Brix) at maturity for consumption | 15.6% | 15.8% |
| General Shape | Ovoid | Ovoid |
| Cross sectional shape | Circular | Circular |
| Shape at Stylar End | Strongly blunt protruding | Slightly blunt protruding |
| Skin: Hairiness | Present | Present/downy |
| VINE | | |
| Shoots: | | |
| Color | 144B | 144B |
| Texture | Smooth | Smooth |
| Stem: | | |
| Colour-upper | 177A | 165A |
| Colour-lower | 199A | 199A |
| Mean diameter | 9.5 mm | 9.0 mm |
| Texture | Smooth | Smooth |
| Lenticel (if present) | Present | Present |
| LEAF: | | |
| Colour-upper | 147A | 144A |
| Colour-lower | 148B | 144B |
| Shape | Orbiculate | Broadly Orbiculate |
| Length | 124 mm | 146 ± 15.9 mm |
| Width | 151 mm | 147 ± 21.7 mm |
| Apex | Acute | Acuminate |
| Base | Cordate | Cordate |
| Margin | Ciliate | Ciliate |
| Texture | Glabrous | Glabrous |
| FLOWER | | |
| Inflorescence: | | |
| Predominant number of flowers | 3 | 3 |

TABLE 1-continued

Comparison With Similar Variety.
Observations made under New Zealand Growing Conditions

| Characteristic | HORT16A | X78 |
|---|---|---|
| Petiole: | | |
| Length | 103 mm | 70.8 ± 11.9 mm |
| Colour | 145B | 182B |
| Pedicel: | | |
| Length | 27.1 mm | 38 mm |
| Colour | 151A | 145A |
| Hairs | Present | Present |
| Length of hairs | Very short | Very short |
| Flower: | | |
| Coloration of petals | Bi-coloured | Bi coloured |
| Primary Colour | White 155B | White 155C |
| Secondary colour base of petal | Green 144D | Green 145B |
| Diameter | 51 mm | 51 mm |
| Arrangement of Petals | Overlapping | Overlapping |
| Mean number of petals/flower | 6 | 7 |
| Mean length of petals | 28.8 mm | 23.6 mm |
| Mean width of petals | 23.9 mm | 18.8 mm |
| Petal ratio of length to width | 1.21 | 1.25 |
| Petal shoulder | Present | Present |
| Filament colour | Green/White 157A | Green/White 157A |
| Anther colour | Yellow 16C | Burnt orange 17A |
| Attitude of styles | Semi erect | Semi erect |
| Curvature of styles | Absent | Absent |
| Colour of styles | White 155D | White 155A |
| Amount of hair on ovary | Dense | Dense |
| Colour of ovary | White 157B | White 157A |
| Number of sepals | 6-7 | 6-8 |
| Colour of sepal | Green 148D | Green 148C |
| Length of sepals | | |
| Range | 8.7-12.4 mm | 9.5-13.8 mm |
| Mean | 11.4 mm | 11.2 mm |
| Sepal diameter | 9.1 mm | 4.9 mm |
| Flower Opening | Mid October | Early October |
| Vegetative bud break | Early September | Mid August |
| Plant/fruit disease & pest resistance | None | None |
| Plant hardiness zone or heat/cold resistance | Not Known | Not known |

Color references are in accord with the R.H.S. Colour Chart, the Royal Horticultural Society, London, 2001

The most striking differences between 'Skelton X78' and 'HORT16A' are the dates of vegetative bud break, flower opening, and the date of fruit maturity. 'Skelton X78' has a vegetative bud break in mid-August several weeks earlier than 'HORT16A.' 'Skelton X78' flowers open earlier than 'HORT16A' in early October, in comparison to mid October. In addition, the harvest dates of 'Skelton X78' are approximately two weeks prior to that of 'HORT16A' in late April instead of early May.

The embodiments of the invention in which an exclusive property or privilege is claimed are defined as follows:

1. A new and distinct kiwi plant of the species *A. chinensis* substantially as herein described and illustrated.

* * * * *